United States Patent [19]

Benajam

[11] Patent Number: 4,687,638

[45] Date of Patent: Aug. 18, 1987

[54] DEVICE FOR DETECTING AND QUANTIFYING AGGLUTINATES

[76] Inventor: Alain C. A. Benajam, 36 avenue Karl Marx, 93000 BOBIGNY, France

[21] Appl. No.: 781,210

[22] Filed: Sep. 30, 1985

Related U.S. Application Data

[63] Continuation of Ser. No. 542,198, Oct. 14, 1983, abandoned.

[30] Foreign Application Priority Data

Oct. 14, 1982 [FR] France .................................. 82 17635

[51] Int. Cl.[4] ..................... G01N 21/13; G01N 31/02; G01N 33/48; G01N 35/04
[52] U.S. Cl. ........................................ 422/73; 422/64; 435/312; 435/316; 436/45; 436/805
[58] Field of Search ................ 422/64, 65, 73, 72; 436/805, 807, 45, 74; 435/291, 312, 316

[56] References Cited

U.S. PATENT DOCUMENTS

| | | | |
|---|---|---|---|
| 3,193,358 | 7/1965 | Baruch | 422/64 |
| 3,488,156 | 1/1970 | Good et al. | 422/73 |
| 3,489,525 | 1/1970 | Natelson | 422/64 |
| 3,607,099 | 9/1971 | Scordato et al. | 422/73 |
| 3,636,777 | 1/1972 | Frank et al. | 422/64 |
| 3,790,346 | 2/1974 | Ritchie | 422/73 |
| 3,883,308 | 5/1975 | Matte | 436/809 |
| 4,285,906 | 8/1981 | Meltzer et al. | 422/73 |
| 4,363,245 | 12/1982 | Schmid | 198/778 |
| 4,387,164 | 6/1983 | Hevey et al. | 436/45 |
| 4,459,265 | 7/1984 | Berglund | 422/65 |

FOREIGN PATENT DOCUMENTS 0046430 2/1982 European Pat. Off. .

Primary Examiner—Barry S. Richman
Assistant Examiner—C. M. Delahunty
Attorney, Agent, or Firm—Fisher, Christen & Sabol

[57] ABSTRACT

The invention relates to a device for detecting and quantifying agglutinates. According to the invention, the reactions take place in pits in a transparent disc and the axis of said disc may move at right angles to an observation device. The invention is more particularly applicable to immunohaematology.

7 Claims, 8 Drawing Figures

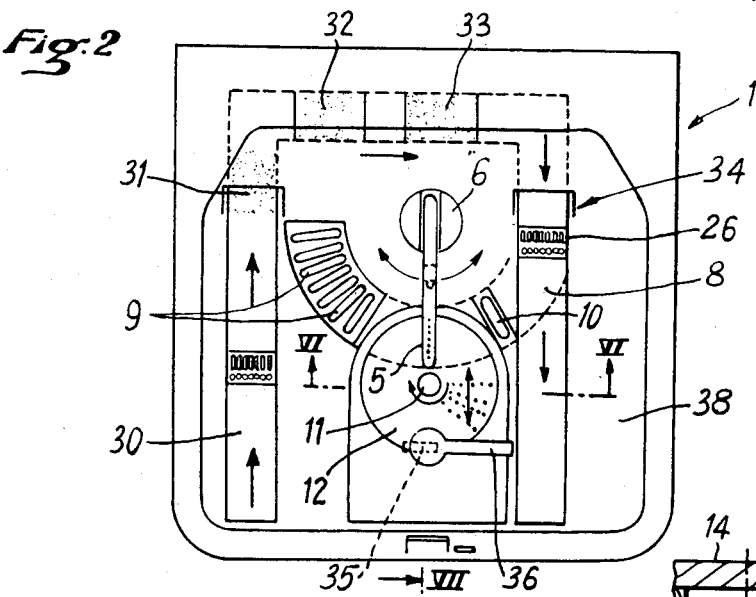
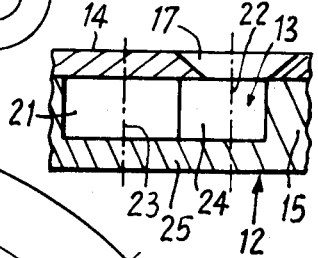
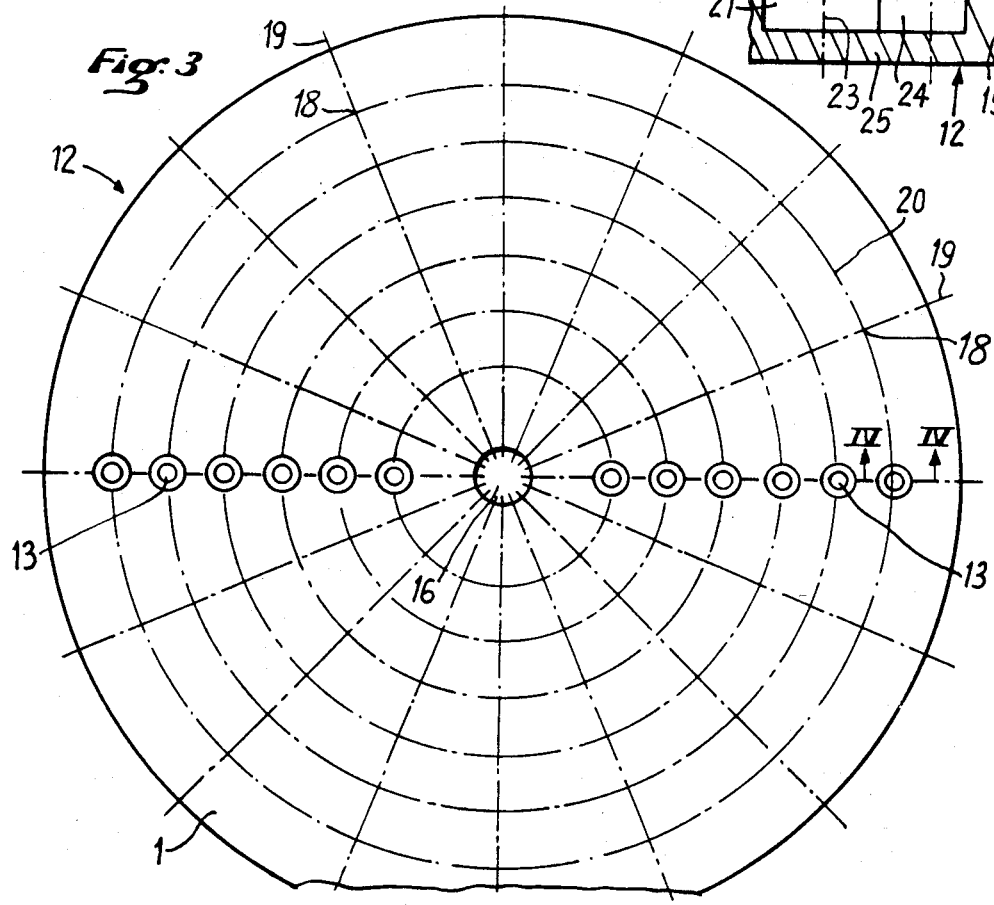

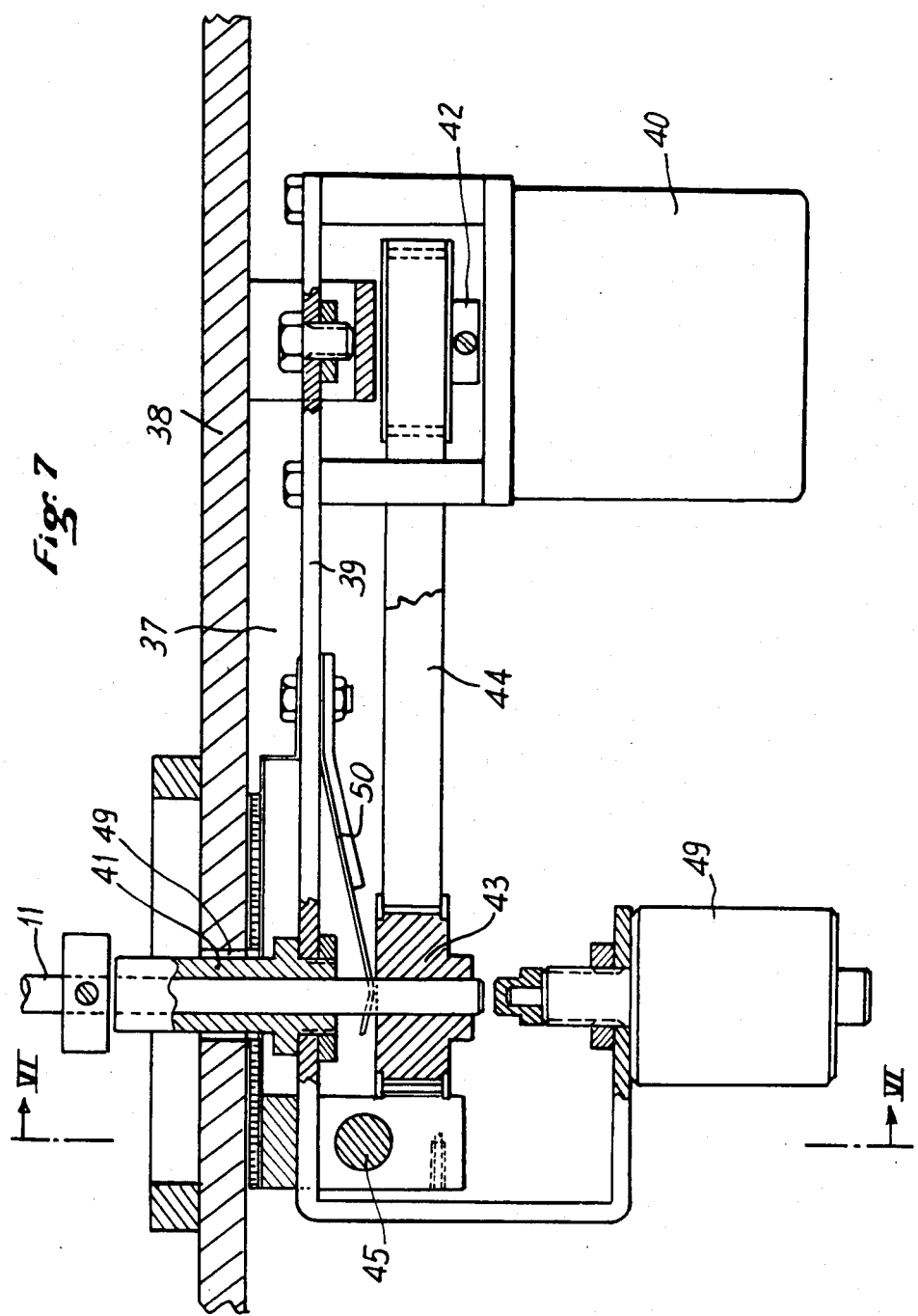

DEVICE FOR DETECTING AND QUANTIFYING AGGLUTINATES

This application is a continuation of application Ser. No. 542,198, filed 10-14-83, now abandoned.

BACKGROUND AND SUMMARY OF THE INVENTION

The present invention relates to a device for the detection and quantification of agglutinates capable of being formed, under the action of at least one reagent, by particles in suspension in a liquid.

It may be used whenever agglutinates are to be detected and quantified. However, it is particularly applicable in immunohaematology, particularly for the purpose of determining blood groups. In fact, it is known that blood groups are determined by seeking the existence in the blood of erythrocytic antigens. The immunocytological reactions, in the face of an antigen of a specific group, are translated by a phenomenon of agglutination of the red blood corpuscles if the latter belong to another group. These red cells may form either uniform agglutinates without free red cells, or some large agglutinates or a large number of small agglutinates.

Although the present invention is not limited in its applications to immunohaematology, it will be descibed hereinafter with more specific reference to this particular application.

A device for the detection and quantification of agglutinates includes a photodetector, a rotatable and translatable support comprising a transparent disc having pits therein, a pivotably supported syringe support which is automatically actuable to draw sample liquids and to dispense sample liquids into pits in the disc, such that each pit can be scanned by the photodetector having for example n detector elements across, and scanning each pit at a plurality of locations (for example, in step-by-step motion of the disc over the photodetector, an n number of times). The agglutinates are capable of being formed under the action of at least one liquid reagent by particles in suspension in doses of liquids to be tested which are contained in recipients formed in the rotatable support. The device comprises a radially disposed arrangement of a plurality n of photosensitive elements. The transparency of the bottoms of said recipients containing the agglutinates permits light passing through said bottoms of said recipients, the light being supplied by a light source overlying the rotatable support.

Said recipients are formed by pits distributed along radii of the transparent horizontal disc support and is adapted to rotate about the vertical axis of the disc. The spindle and disc are movable in m steps past the arrangement 35 n times for each recipient, thereby sensing a total of n×m locations of each individual recipient. An oscillating arm movable about a vertical axis by a support member, and having syringes for taking and restituting liquid doses is provided, to take such doses from reservoirs of reagents located within the range of movement of the oscillating arm. The arm takes liquids to be tested and deposits the liquid into said pits in the rotatable disc. The linear arrangement of photosensitive elements is permanently disposed at right angles to a diameter of the transparent disc and is in a plane parallel to a plane containing a lower surface of the disc. The axis of rotation of the disc is mounted to move in translation at right angles to said linear arrangement of photosensitive elements so that each recipient can be scanned at n×m points by appropriate translation of the disc relative to the photodetector elements.

Via its means for taking and restituting liquid doses, which may for example be syringes, the oscillating arm may thus introduce into each pit in the rotating disc a liquid to be tested and the corresponding reagent. After reaction, each pit is examined by the photosensitive element arrangement in the course of translation of the axis of the disc, the amplitude of which translation is sufficient for all the pits of a radius of the disc to be observed, each in m steps.

The oscillating arm advantageously bears as many taking and restituting means as a radius of the disc comprises pits, with the result that the oscillating arm fills all the pits of a radius at one time.

In an advantageous embodiment, the linear arrangement of photosensitive elements is disposed at right angles to the vertical plane passing through the vertical axes of the transparent disc and the oscillating arm, on the side of the disc axis opposite said oscillating arm, so that the disc must make a rotation through 180° for a radius of pits filled with doses of liquids to be tested and with reagent to be read by said arrangement.

The reservoirs of reagents are preferably disposed permanently on one side of the vertical plane defined by the vertical axes of the oscillating arm and the disc, whilst the reservoirs of liquids to be tested are associated with conveyor means advancing them step by step, parallel to this vertical plane, but on the side opposite said reservoirs of reagents.

The arrangement of photosensitive elements may be of the type constituted by a bar of charge coupled diodes, generally designated by the letters CCD, DTC or CCPD. According to the invention, in which a rectilinear bar of n charge coupled devices is used, observation is effected with a view to detecting the possible agglutinates and during the relative movement of each transparent bottom of the recipient in m spaced apart, parallel positions of said bar, so as to form n×m points of observation distributed over a rectangular or square surface occupying the major part of the surface of said bottom. Of course, n may be chosen to be equal to m and the distance between two consecutive positions of observation of the bar is arranged to be equal to the distance between two CCDs of the bar. Thus, a square surface of the transparent bottom is totally covered. For example, the rectilinear bar comprises 256 CCD photodiodes, each having a definition of 25 $\mu_m$, the video information being digitized in 256 grey levels, and the analyzed image represents a square centred on said transparent bottom and formed by 256 scans spaced apart by 25 $\mu_m$.

For observing the agglutinates and for each recipient, n×m measures are thus obtained, distributed in m scans of n points.

The invention will be more readily understood on reading the following description with reference to the accompanying drawings, in which:

BRIEF DESCRIPTION OF THE DRAWING

FIG. 2 is a simplified plan view of the device according to the invention.

FIG. 3 is a plan view of a pitted disc used in the device according to the invention.

FIG. 4 is a section along line IV—IV of FIG. 3.

FIGS. 6 and 7 are sections respectively along lines VI—VI and VII—VII of FIG. 2.

In these Figures, like references designate like elements.

DETAILED DESCRIPTION OF THE INVENTION

Figure 1:
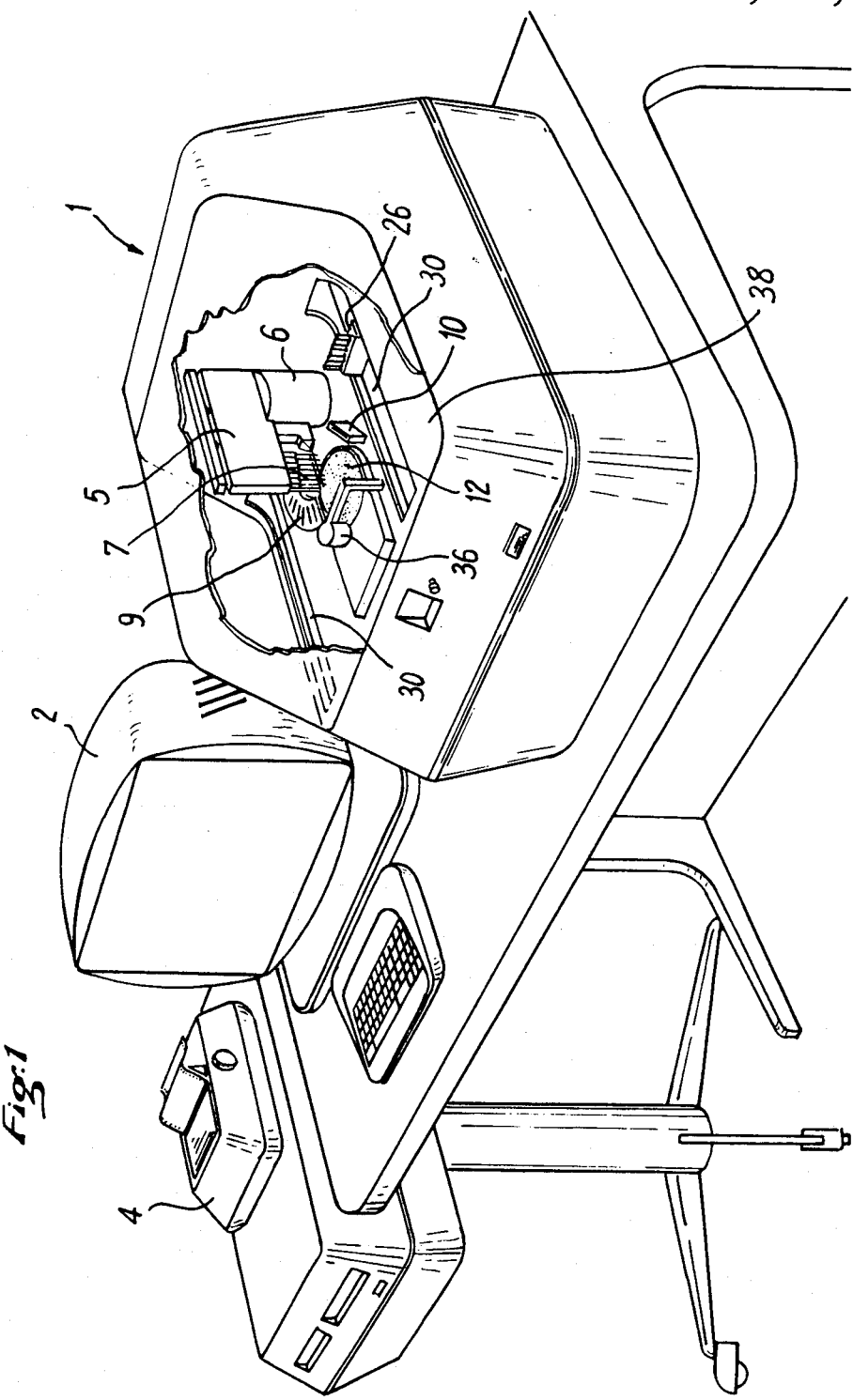
FIG. 1 is an overall view in perspective, with parts torn away, of an installation with the device according to the invention.

Referring now to the drawings, the installation for recognizing blood groups, shown in FIG. 1, comprises a device 1 according to the invention for detecting and quantifying agglutinates, associated with a display device 2, a control device 3 and a printing device 4. The whole of the installation is controlled by a microprocessor (not shown) according to a process which is not described further hereunder.

As also shown in FIG. 2, the device 1 according to the invention comprises a horizontal oscillating arm 5 capable of rotating about a vertical axis of a member 6. The arm 5 bears a plurality of vertical syringes 7, each syringe having a piston as is well-known in the syringe art. The pistons of the syringes 7 (pistons not shown) may be actuated to draw in or drive out a liquid. When arm 5 oscillates about the vertical axis of the member 6, the syringes 7 sweep over an annular zone 8.

In this annular zone 8 there are provided recipients 9 containing reagents from each of which the vertical syringes 7 may take a reagent, and a recipient 10 for rinsing.

Furthermore, device 1 comprises a vertical spindle 11 capable of rotating a disc 12 of transparent material in which pits 13 are made. For example, as shown in FIGS. 3 and 4, the disc 12 comprises an upper disc 14 and a lower disc 15 superposed and assembled for example by adhesion. Discs 14 and 15 are made of a transparent synthetic material and are provided at their centre with holes 16 to allow passage of the rotating drive spingle 11 when the discs 1 and 2 are superposed and joined together.

The upper disc 14 is provided with a plurality of through holes 17 whose axes 22 at right angles to the plane of the disc 14 are distributed at a plurality of points 18 lying at the intersection of radii 19 and concentric circles 20. Furthermore, the top of each hole 17 is flared out.

For the purpose of clarity of the drawing, only a few holes 17 have been shown in FIG. 3.

The lower transparent disc 15 comprises a plurality of blind holes 21 of which axes 23 are distributed at a plurality of points lying at the intersection of radii and concentric circles and are offset with respect to axes 22. The blind holes 21 in the lower disc 15 communicate with holes 17 by a flat-bottomed communicating passage 24, which is sufficiently elongated for the upper edge of the funnels 17 to lie outside the recipient holes 21 or at least to clear on the bottom thereof a field of vision 25 covering substantially the major part of said bottom.

The annular zone 8 scanned by movement of the arm 5 by syringes 7 sweeps above and across the disc 12 so that it is possible to fill all of the pits 13 (or recipient 13) disposed on a radius 19 of the disc 12, with doses of reagents coming from reservoirs 9 by introducing the needles of the syringes 7 into the corresponding funnels 17, the liquid then passing through holes 17 and 24 to reach blind hole 21. In the same way, it is possible to introduce into recipients 13 doses of liquids coming from reservoirs 26 located in zone 8. When stirring or centrifugation is necessary, it suffices to subject the disc 12 to such movement as required for stirring or centrifugation and, since the holes 21 are obturated by disc 14, there is no risk of the liquid contained in recipients 13 escaping to the outside of the recipients.

Figure 5:
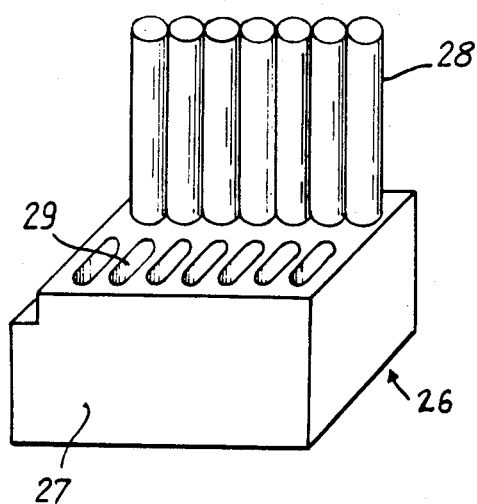
FIG. 5 shows in perspective a sample holder for the device according to the invention.

Reservoirs 26 are constituted (cf. FIG. 5) by transparent blocks 27 removably supporting tubes 28 which contain blood samples coming from donors, and in which recesses 29 are optionally formed which contain dilutions of the liquids of said tubes.

Reservoirs 26 are introduced into device 1 by a conveyor 30 which passes them successively to different treatment stations 31, 32 and 33, as shown in FIG. 2, and then to station 34 where syringes 7 of arm 5 may selectively withdraw the liquid which they contain.

In this way, each pit 13 in disc 12 may serve as recipient for reaction between a liquid coming from a reservoir 26 and a reagent coming from a reservoir 9 by successive operations of the syringes 7 mounted on the pivotable arm 5.

Figure 8:
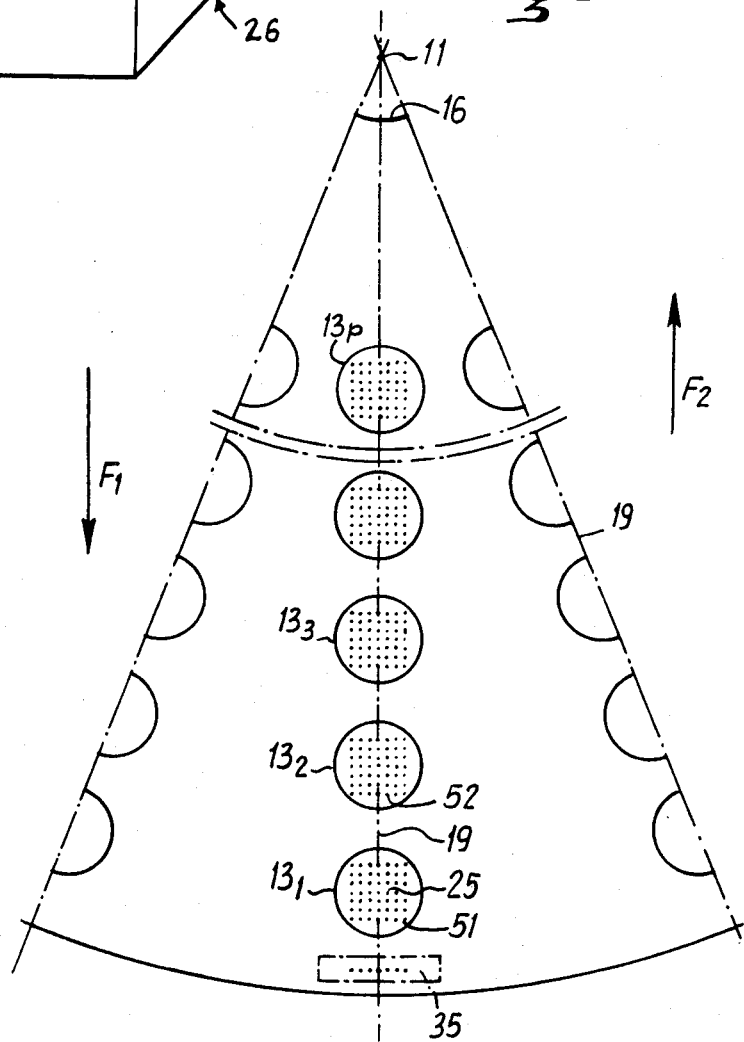
FIG. 8 schematically illustrates the process of reading the agglutinates.

To examine the result of agglutination which may result from such reactions, device 1 includes a bar 35 (shown in dotted outline in FIGS. 2 and 8) of CCD diodes, disposed beneath disc 12 opposite an illuminating device 36 (shown in FIG. 2). Bar 35 and illuminating device 36 are disposed diametrically opposite arm 5 with respect to axis the rotatable member 11, and bar 35 is oriented at a right angle to a vertical plane defined a plane containing the axes of member 6 and 11.

Bar 35 examines by passage of light through the transparent bottom 25 of each pit 13 by m observations, each separate observation being made by a movement of the disc 12 which is offset by a step due to translational movement of the member 11 in a direction parallel to a plane containing the disc 12. For all pits 13 at a radius 19 of disc 12 to be each examined in m steps, the spindle 11 of said disc 12 is moved in horizontal translation parallel to said disc 12 and, at right angles to a vertical plane containing said bar 35.

Figure 6:
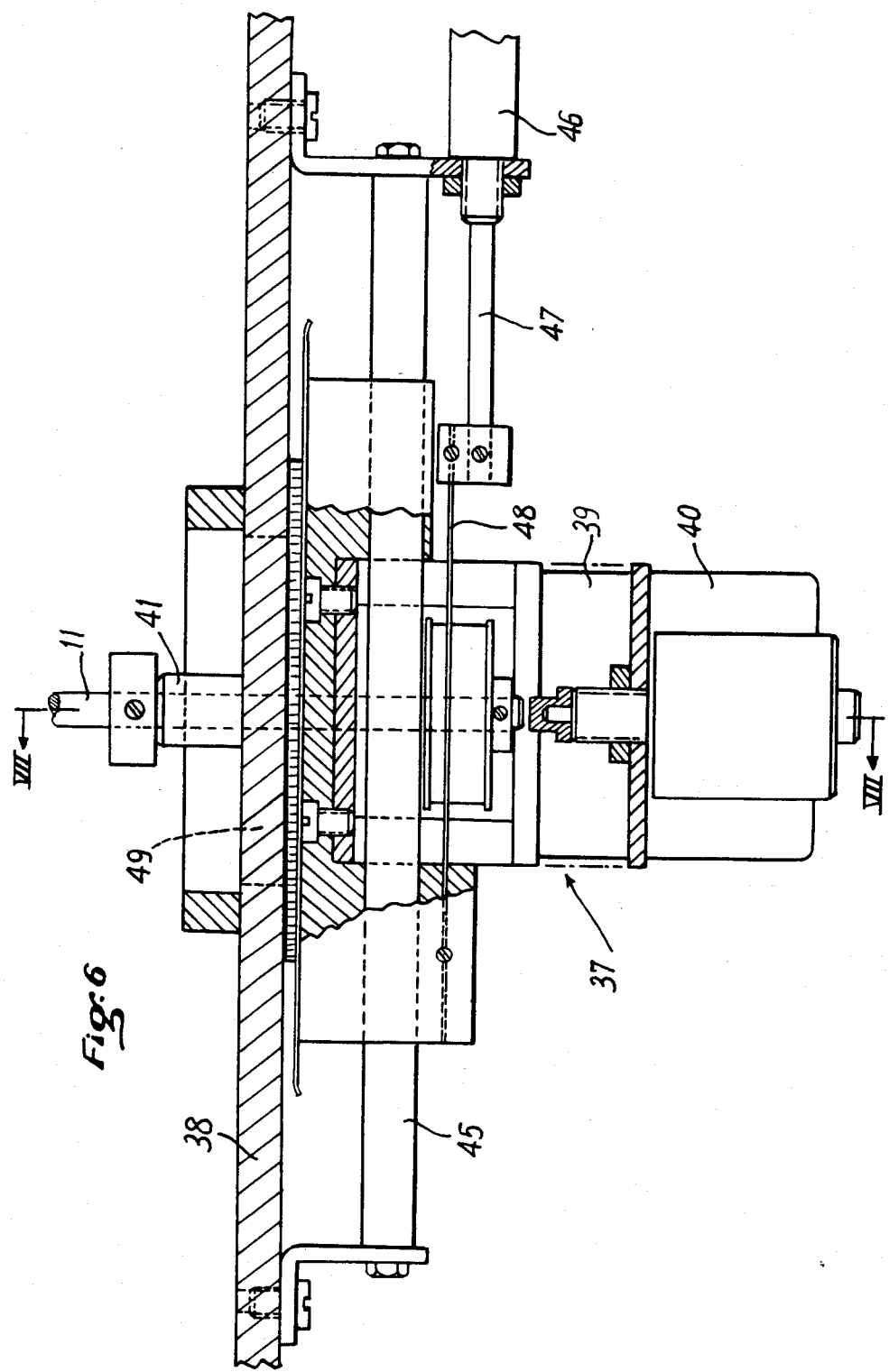

To this end, FIGS. 6 and 7 show that spindle 11 of disc 12 is fixed to a carriage 37 which is movable with respect to a base plate 38 of the device. This carriage 37 includes a frame 39 supporting a motor 40 and a smooth bearing 41 for spindle 11. The driven shaft of motor 40 rotates a pulley 42 which is connected to a pulley 43 fixed on spindle 11, via a synchronous belt 44. Carriage 37 is guided in translation by a rail 45 and it moves under the action of a jack 46, having a rod 47 which is connected to carriage 37 by a rod 48.

In this way, spindle 11 is slidable in a slot 49 in the base plate 38 parallel to rail 45 and at right angles to a vertical plane containing the bar 35 of CCD diodes.

The carriage 37 can moreover supporta vibrating means 49 adapted episodically to animate the spindle 11 by a reciprocating movement parallel to the axis of the spindle 11, against the action of a spring 50, in order to selectively stir the liquid contained in the pits 13 in disc 12.

When pits $13_1$ to $13_p$ of radius 19 lying in the plane coplanar with the vertical axes of members 6 and 11 are to be read by the arrangement 35 in order to detect and quantify the agglutinations, indicated as field 25 having an outer limit 52, (cf. FIG. 8), disc 12 is advanced by jack 46 in the direction of arrow $F_1$ for arrangement 35 to be plumb with (directly beneath) the outer limit 51 of field 25 of the bottom of the first pit $13_1$. Then, the jack is displaced by step m times for the n photosensitive elements of arrangement 35 to examine said field 25 at n×m points. When field 25 of pit $13_1$ has been read, jack 46 displaces spindle 11, still in direction $F_1$, so that the outer limit 52 of field 25 of the bottom of second pit $13_2$ comes plumb with the photosensitive elements of arrangement 35. This second pit $13_2$ is read in identical manner and the process continues until reading of pit $13_p$ has been completed. Thereafter jack 46 returns spindle 11 into its initial position (arrow $F_2$).

It is readily apparent from the figures and from the description hereinabove that all of the elements n×m can be read by any combination of a rotation of the disc 12 about spindle 11 and step advancement of the spindle 11 linearly along a radius of the disc 12 under the action of the jack 46.

What is claimed is:

1. A device for the detection and quantification of agglutinates, which agglutinates are capable of being formed under the action of at least one liquid reagent by particles in suspension in doses of liquids to be tested, comprising:

(A) a horizontal disc positioned and arranged for rotation about a spindle having a first vertical axis, said horizontal disc having a plurality of pits disposed on a first surface thereof to form uniform linear arrangements of pits along radii of said disc, the bottom of each of said plurality of pits being transparent;

(B) an oscillating arm rotatable about a second vertical axis and having as many taking and restituting means as there are pits disposed along each one of said radii, said taking and restituting means being positioned and arranged on said oscillating arm for taking doses of liquid reagents and of liquids to be tested from corresponding reservoirs of reagents and liquids to be tested and for dispensing simultaneously such doses into a radial linear arrangement of pits in the rotating disc;

(C) a horizontal fixed linear arrangement of a plurality n of photosensitive elements;

(D) a fixed light source located on an opposite side of the horizontal plane of said disc than said horizontal fixed linear arrangement, said linear arrangement of photosensitive elements and said light source being positioned and arranged with respect to said disc so that light from the light source can pass through an adjacent one of said plurality of pits to said linear arrangement of photosensitive elements;

(E) a means for horizontally moving said disc step-by-step m times in a direction generally at right angles to said linear arrangement of photosensitive elements, such that the amount of light from said light source passing through said bottom of each of said pits is detected m times by each of said n photosensitive elements, so as to form for each said bottom a total of n×m points of detection distributed over a rectangular region, said rectangular region occupying a major part of the surface of the bottom of each pit;

(F) means for controllably rotating said horizontal disc about said first vertical axis to successively bring each of said linear arrangements of pits into position for observation by said horizontal fixed linear arrangement; and said means for horizontally moving said disc including a carriage mounted on a rail for sliding movement thereon in the horizontal direction, said spindle being mounted on said carriage for rotation relative to said carriage, and said means for controllably rotating said disc comprising a motor supported on said carriage and positioned and arranged to rotatably drive said spindle.

2. The device of claim 1 wherein said linear arrangement of photosensitive elements is disposed at right angles to a vertical plane passing through both said first vertical axis of said spindle and said second vertical axis of said oscillating arm, and is located on the side of said first vertical axis of said spindle opposite said oscillating arm.

3. The device of claim 1 wherein said arrangement of photosensitive elements is a bar of CCD diodes.

4. The device of claim 1 where said means for horizontally moving said disc further comprises a jack positioned and arranged to move said carriage along said rail.

5. The device of claim 1 wherein said spindle of said disc is mounted in a smooth bearing fixed to said carriage, and wherein said device further includes a vibrating means positioned and arranged to cause said spindle to vibrate about a longitudinal axis.

6. The device of claim 1 further comprising reservoirs of reagents disposed permanently on one side of a vertical plane defined by said second vertical axis of said oscillating arm and said first vertical axis of said spindle and reservoirs of liquids to be tested disposed on an opposite side of said vertical plane.

7. The device of claim 6 further comprising conveyor means and wherein said reservoirs containing the liquids to be tested are mobile and brought to said stations by said conveyor means.

* * * * *

UNITED STATES PATENT AND TRADEMARK OFFICE
CERTIFICATE OF CORRECTION

PATENT NO. : 4,687,638

DATED : August 18, 1987

INVENTOR(S) : Alain C. A. Benajam

It is certified that error appears in the above-identified patent and that said Letters Patent is hereby corrected as shown below:

Title page:

[73] Assignee: Société à Responsabilité Limitée dite:
LE MATERIEL BIOMEDICAL
4 rue de Presbourg, 75116 Paris, FRANCE Signed and Sealed this Eighth Day of March, 1988

Attest:

DONALD J. QUIGG

*Attesting Officer*   *Commissioner of Patents and Trademarks*